(12) United States Patent
Woods et al.

(10) Patent No.: US 6,740,193 B2
(45) Date of Patent: May 25, 2004

(54) GEM-DIESTERS AND EPOXIDIZED DERIVATIVES THEREOF

(75) Inventors: John G. Woods, Farmington, CT (US); Jianzhao Wang, Ossining, NY (US); Jean M. J. Fréchet, Oakland, CA (US)

(73) Assignee: Henkel Corporation, Rocky Hill, CT (US)

( * ) Notice: Subject to any disclaimer, the term of this patent is extended or adjusted under 35 U.S.C. 154(b) by 47 days.

(21) Appl. No.: 10/032,128

(22) Filed: Dec. 21, 2001

(65) Prior Publication Data

US 2003/0157334 A1 Aug. 21, 2003

(51) Int. Cl.[7] .................. C09J 163/00; B32B 27/38; C07D 301/03; C07C 69/52; C08G 63/52
(52) U.S. Cl. .................. 156/330; 156/344; 549/523; 549/547; 560/128; 560/190; 560/193; 560/201; 560/203; 560/205; 560/209; 528/274; 528/297; 528/303; 528/418; 428/413
(58) Field of Search .................. 560/128, 190, 560/193, 201, 203, 205, 209; 549/523, 547; 156/330, 344; 524/528; 523/400, 412; 528/274, 297, 303, 418; 428/413

(56) References Cited

U.S. PATENT DOCUMENTS

| | | | | |
|---|---|---|---|---|
| 3,275,661 A | * | 9/1966 | Widmer et al. | 549/547 |
| 3,293,220 A | * | 12/1966 | Minami et al. | 525/400 |
| 5,512,613 A | | 4/1996 | Afzali-Ardakani et al. | 523/443 |
| 5,552,070 A | * | 9/1996 | Schafer et al. | 508/224 |
| 5,560,934 A | | 10/1996 | Afzali-Ardakani et al. | 424/497 |
| 5,710,328 A | * | 1/1998 | Spivey et al. | 562/599 |
| 5,744,637 A | * | 4/1998 | Tustin et al. | 560/238 |
| 5,932,682 A | | 8/1999 | Buchwalter et al. | 528/94 |
| 5,948,922 A | * | 9/1999 | Ober et al. | 549/547 |
| 5,973,033 A | | 10/1999 | Ober et al. | 523/443 |
| 6,008,266 A | | 12/1999 | Kuczynski et al. | 522/31 |
| 6,110,955 A | * | 8/2000 | Nudelman et al. | 514/411 |
| 6,255,500 B1 | * | 7/2001 | Klemarczyk | 549/525 |
| 6,313,327 B1 | * | 11/2001 | Seo et al. | 552/553 |

FOREIGN PATENT DOCUMENTS

EP 125781 A1 * 11/1984 ............ C11D/3/39

OTHER PUBLICATIONS

S. Yang et al., *Chem. Mater.*, 10(6), 1475 (1998).
J.S. Chen et al., *ACS Polymer Preprints*, 41(2), 1842 (2000).
H. Li et al., *ACS PMSE Preprints*, 83, 563 (2000).
S. Buchwalter, et al., *ACS PMSE Preprints*, 72, 450 (1995).
L. Wang and C. Wong, *Journal of Polymer Chemistry, Part A*, vol. 37, 2991 (1997).
Journal of Organic Chemistry of the USSR, Original vol. 21, No. 2, Part 1 (1985).
*Reviews on Heteroatom Chemistry* vol. 9, "A New Strategy in the Synthesis of Epoxy Resins", (1993).

* cited by examiner

*Primary Examiner*—Jeffrey B. Robertson
(74) *Attorney, Agent, or Firm*—Stephen E. Reiter; Foley & Lardner

(57) ABSTRACT

In accordance with the present invention, there are provided gem-diesters and epoxidized derivatives thereof. When cured, thermosets comprising invention gem-diesters and epoxidized derivatives thereof have thermally and/or chemically labile gem-diester groups interspersed throughout the crosslinked network. Thus, thermosets based on invention gem-diesters and epoxidized derivatives thereof can be easily reworked thermally or chemically by treatment with dilute acidic or basic solutions. Further provided by the present invention are adhesive compositions comprising invention gem-diesters and epoxidized derivatives thereof.

65 Claims, 3 Drawing Sheets

US 6,740,193 B2

GEM-DIESTERS AND EPOXIDIZED DERIVATIVES THEREOF

FIELD OF THE INVENTION

The present invention relates to gem-diesters and epoxidized derivatives thereof In a particular aspect, the present invention relates to re-workable adhesive compositions and methods for use thereof.

BACKGROUND OF THE INVENTION

Epoxide resins are widely recognized as one of the most important types of thermosetting materials. Indeed, epoxies have been successfully used in a diverse array of applications, such as, for example, structural materials, adhesives, and coatings. The superior physical properties provided by cured epoxide resins (e.g., adhesive strength, toughness, resistance to degradation), combined with their relatively low cost, have allowed epoxides to displace other thermosetting chemistries in a variety of industries. In particular, epoxide resins have gained acceptance in the microelectronics industry in a variety of packaging applications, due to their low shrinkage upon cure, corrosion resistance, and good electrical properties. Accordingly, epoxies have been used in microelectronic packaging applications such as, for example, encapsulants, die-attach pastes, molding compounds, underfill materials, solder masks, and the like.

However, the very attributes which have allowed epoxies to gain such widespread acceptance in a variety of industries have, in certain respects, become liabilities. For example, in the microelectronics industry, the intractability of cured epoxide resins leaves little margin for error in the packaging of microelectronic components. Indeed, after the epoxide-based packaging material has been cured, it is exceedingly difficult to separate the component from its packaging material without damaging the component. Thus, if any error is detected in the semiconductor package post-cure, the entire assembly must often be discarded. Since the packaging step is the last stage in the manufacture of a microelectronic component, the loss of the component at this stage is especially taxing economically.

Moreover, recent environmental concerns have led to the development of recyclable products in a variety of industries. Traditionally, articles containing epoxide-based thermosetting adhesives have not been compatible with recycling protocols due to the high adhesive strength and intractability of the crosslinked thermoset network. Thus, as demand for recyclable products increases, there is simultaneously an increasing demand for thermosetting compositions which are re-workable (so as to be amenable to recycling protocols) yet maintain desirable properties such as high adhesive strength and toughness.

Epoxides have been developed which impart, at least to some degree, reworkable properties to a thermosetting resin produced therefrom. These epoxides contain labile groups such as secondary and tertiary esters (see C. Ober and H. Koerner, U.S. Pat. No. 5,973,033, S. Yang et al, *Chem. Mater.*, 1998, 10 (6), 1475, J. S. Chen et al, *ACS Polymer Preprints* 2000, 41(2), 1842, H. Li et al *ACS PMSE Preprints* 2000, 83, 563), aliphatic acetals (see A. Afzali-Ardakani et al, U.S. Pat. No. 5,512,613, A. Afzali-Ardakani et al, U.S. Pat. No. 5,560,934, S. Buchwalter et al, U.S. Pat. No. 5,932,682, J. Kuczynski and L. Mulholland, U.S. Pat. No. 6,008,266, S. Buchwalter et al, *ACS PMSE Preprints* 1995, 72, 450), and various carbamates (see L. Wang and C. Wong, *J. Polym. Sci. Part A* 1999, 37, 2991).

While these systems can provide network breakdown under certain conditions, there are several undesirable features associated with their use. Epoxidized secondary and tertiary esters are costly to produce and generally undergo network degradation at lower temperatures than is ideal. Epoxidized aliphatic acetals decompose only very slowly at high temperatures. Epoxidized carbamates are costly to produce and have the added undesirable effect of producing highly toxic isocyanates following thermolysis. In addition, the above classes of epoxy adhesives leave decomposition residues on the circuit board that are difficult to remove and thus make replacement more difficult than is desirable.

Thus, there is a need for reworkable epoxy adhesives are inexpensive to produce, do not generate toxic by-products on decomposition, and leave residues that are easy to clean. The present invention addresses these needs and further provides related advantages as will become apparent upon review of the specification and appended claims.

SUMMARY OF THE INVENTION

In accordance with the present invention, there are provided ethylenically unsaturated gem-diesters and epoxidized derivatives thereof. When cured, thermosets comprising invention ethylenically unsaturated gem-diesters and epoxidized derivatives thereof have thermally and/or chemically labile gem-diester groups interspersed throughout the crosslinked network. Thus, thermosets based on invention compounds can be easily reworked by simply heating the thermoset or by treatment with dilute acidic solutions or dilute basic solutions.

In accordance with a further embodiment of the present invention, there are provided adhesive compositions comprising invention compounds and methods for use thereof.

In additional embodiments of the present invention, there are provided methods for the preparation of epoxidized derivatives of gem-diesters, methods for adhesively attaching a device to a substrate, and methods for removing an adhesively attached device from a substrate.

In still further embodiments of the present invention, there are provided assemblies comprising first article(s) reversibly adhered to second article(s).

DETAILED DESCRIPTION OF THE INVENTION

Figure 1:
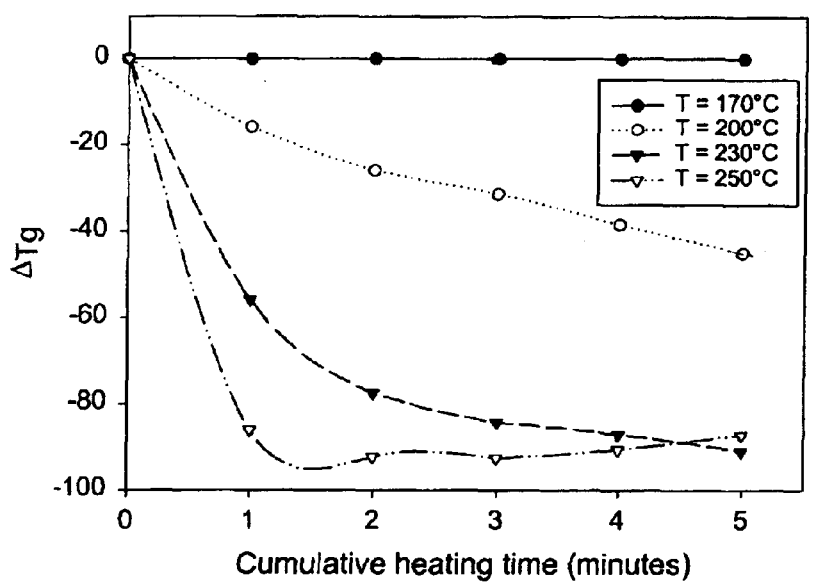
FIG. 1 illustrates the decomposition of anhydride cured formulation comprising invention compound 2 as a function of heating time at various temperatures (initial Tg=152° C.).

In accordance with the present invention, there are provided ethylenically unsaturated gem-diesters having the structure:

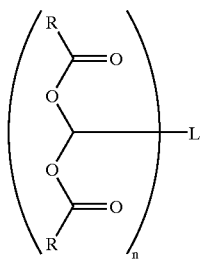

wherein:
L is optionally substituted hydrocarbyl, hydrocarbylene, heteroatom-containing hydrocarbyl, or heteroatom-containing hydrocarbylene,
each R is independently selected from optionally substituted hydrocarbyl or heteroatom-containing hydrocarbyl, and
n is 1 or 2,
with the proviso that said gem-diester contains at least two units of ethylenic unsaturation.

As employed herein, "hydrocarbyl" refers to alkyl, substituted alkyl, cycloalkyl, substituted cycloalkyl, alkenyl, substituted alkenyl, alkynyl, substituted alkynyl, aryl, substituted aryl, and the like.

As employed herein, "alkyl" refers to hydrocarbyl radicals having 1 up to about 20 carbon atoms, preferably 2–10 carbon atoms; and "substituted alkyl" comprises alkyl groups further bearing one or more substituents selected from hydroxy, alkoxy, mercapto, cycloalkyl, substituted cycloalkyl, heterocyclic, substituted heterocyclic, aryl, substituted aryl, heteroaryl, substituted heteroaryl, aryloxy, substituted aryloxy, halogen, cyano, nitro, amino, amido, C(O)H, acyl, oxyacyl, carboxyl, carbamate, sulfonyl, sulfonamide, sulfuryl, and the like.

As employed herein, "cycloalkyl" refers to cyclic ring-containing groups containing in the range of 3 up to about 8 carbon atoms, and "substituted cycloalkyl" refers to cycloalkyl groups further bearing one or more substituents as set forth above.

As employed herein, "alkenyl" refers to straight or branched chain hydrocarbyl groups having at least one carbon-carbon double bond, and having in the range of 2 up to about 12 carbon atoms, and "substituted alkenyl" refers to alkenyl groups further bearing one or more substituents as set forth above.

As employed herein, "cycloalkenyl" refers to cyclic ring-containing groups containing in the range of 3 up to about 8 carbon atoms, wherein the cyclic ring-containing group contains at least one carbon-carbon double bond. "Substituted cycloalkenyl" refers to cycloalkenyl groups further bearing one or more substituents as set forth above. Cycloalkenyl groups as defined herein also refer to bicycloalkenyl groups, such as, for example, 2.2.1.-bicycloheptene, and the like.

As employed herein, "alkynyl" refers to straight or branched chain hydrocarbyl groups having at least one carbon-carbon triple bond, and having in the range of 2 up to about 12 carbon atoms, and "substituted alkynyl" refers to alkynyl groups further bearing one or more substituents as set forth above.

As employed herein, "aryl" refers to aromatic groups having in the range of 6 up to about 14 carbon atoms and "substituted aryl" refers to aryl groups further bearing one or more substituents as set forth above.

As employed herein, "hydrocarbylene" refers to divalent moieties, such as, for example, alkylene, substituted alkylene, cycloalkylene, substituted cycloalkylene, alkenylene, substituted alkenylene, alkynylene, substituted alkynylene, arylene, substituted arylene, and the like.

As employed herein, "alkylene" refers to divalent hydrocarbyl radicals having 1 up to about 20 carbon atoms, preferably 2–10 carbon atoms; and "substituted alkylene" comprises alkylene groups further bearing one or more substituents as set forth above.

As employed herein, "cycloalkylene" refers to divalent cyclic ring-containing groups containing in the range of 3 up to about 8 carbon atoms, and "substituted cycloalkylene" refers to cycloalkylene groups further bearing one or more substituents as set forth above.

As employed herein, "alkenylene" refers to divalent, straight or branched chain hydrocarbyl groups having at least one carbon-carbon double bond, and having in the range of 2 up to about 12 carbon atoms, and "substituted alkenylene" refers to alkenylene groups further bearing one or more substituents as set forth above.

As employed herein, "alkynylene" refers to divalent straight or branched chain hydrocarbyl groups having at least one carbon-carbon triple bond, and having in the range of 2 up to about 12 carbon atoms, and "substituted alkynylene" refers to alkynylene groups further bearing one or more substituents as set forth above.

As employed herein, "arylene" refers to divalent aromatic groups having in the range of 6 up to about 14 carbon atoms and "substituted arylene" refers to arylene groups further bearing one or more substituents as set forth above.

As employed herein, "heteroatom-containing hydrocarbyl" and "heteroatom-containing hydrocarbylene" refers to hydrocarbyl and hydrocarbylene moieties which additionally contain heteroatoms such as, for example, N, O, S, and the like.

As employed herein, "unit of ethylenic unsaturation" refers to unsaturation comprising localized (i.e., non-aromatic) carbon-carbon double bonds, as shown below:

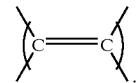

In one aspect of the invention, L is an optionally substituted aryl or arylene, such as, for example, phenyl, naphthyl, anthracyl, and the like. Preferably, L is an optionally substituted phenyl. In a most preferred aspect of the invention, L has the following structure:

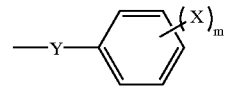

wherein:
Y is optional and if present is $C_1$ to $C_6$ alkylene or alkenylene,
X, when present, is alkyl, alkenyl, haloalkyl, hydroxy, alkoxy, alkenyloxy, mercapto, heterocyclic, aryl, alkaryl, heteroaryl, aryloxy, halogen, cyano, nitro, amino, amido, C(O)H, acyl, oxyacyl, carboxyl, carbamate, sulfonyl, sulfonamide, or sulfuryl, and
m is 0–5.

In a preferred aspect of this embodiment of the invention, X is alkyl, aryl, alkaryl, alkoxy, alkenyl, alkenyloxy, or halogen.

As used herein, "alkaryl" refers to an aryl group bearing an alkyl substituent.

As used herein, "alkenyloxy" refers to an alkenyl moiety wherein one or more of the methylene units of the alkenyl moiety has been replaced with an oxygen atom.

In another aspect of the present invention, L is an optionally substituted aliphatic hydrocarbyl, such as, for example, alkyl, alkenyl, cycloalkyl, cyloalkenyl, alkynyl, and the like.

In a further aspect of the invention, R is an optionally substituted alkyl, alkenyl, cycloalkyl, or cycloalkenyl. In a preferred aspect, R is cycloalkenyl. In a presently most preferred aspect, R is cyclohexenyl.

In another embodiment of the invention, there are provided gem-diesters wherein n is 1, thereby resulting in gem-diesters having two R groups per molecule, wherein each R is independently as defined above, with the proviso that the gem-diesters contain at least two units of ethylenic unsaturation. In an alternative aspect of this embodiment, there are provided gem-diesters wherein n is 2, thereby resulting in gem-diesters having four R groups per molecule, wherein each R is independently as defined above, with the proviso that the gem-diesters contain at least two units of ethylenic unsaturation. Exemplary structures of invention gem-diesters wherein n is 1 and 2 are shown below:

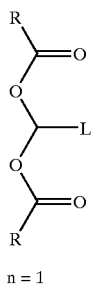
n = 1

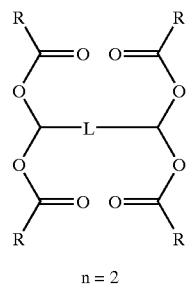
n = 2

In accordance with another embodiment of the present invention, there are provided epoxidized derivatives of the above-described gem-diesters, wherein at least one R group of the gem-diester is epoxidized. Invention epoxidized gem-diesters can be readily prepared in a variety of ways, e.g., invention epoxidized gem-diesters are readily prepared in two steps, as shown, for example, in Scheme 1.

Scheme 1

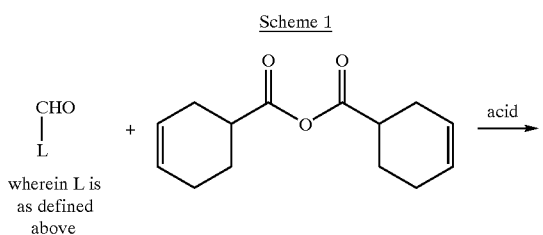

wherein L is as defined above

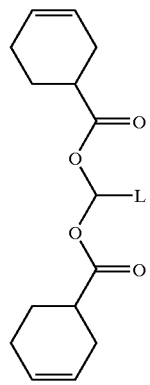

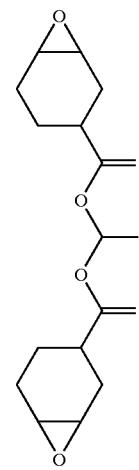

In the first step, an aldehyde reacts with an ethylenically unsaturated anhydride under acid catalysis to form an ethylenically unsaturated gem-diester. Oxidation of the ethylenic unsaturation in the second step affords the epoxidized gem-diester.

Those of skill in the art readily recognize that invention gem-diesters may be substituted in a variety of ways. For example, in the exemplary structure depicted in Scheme 1 (wherein each R group is a cycloalkenyl ring), it is understood that each R group may be independently substituted with a variety of substituents such as, for example, alkyl, hydroxy, alkoxy, mercapto, cycloalkyl, substituted cycloalkyl, heterocyclic, substituted heterocyclic, aryl, substituted aryl, heteroaryl, substituted heteroaryl, aryloxy, substituted aryloxy, halogen, cyano, nitro, amino, amido, C(O)H, acyl, oxyacyl, carboxyl, carbamate, sulfonyl, sulfonamide, sulfuryl, and the like. Moreover, those of skill in the art readily recognize that substituents may be introduced at any step in the synthesis outlined in Scheme 1, so long as the substituent(s) is compatible with the reaction conditions used to produce invention gem-diesters and epoxidized derivatives thereof.

A variety of acids well-known to those skilled in the art may be used to catalyze the first reaction in Scheme 1, such as, for example, the inorganic acids $H_2SO_4$, $PCl_3$, and the like, or organic acids such as sulfonic acids, and the like. In addition, latent acids such as, for example, N-halosuccinimides, and the like, may also be used to catalyze the first reaction in Scheme 1. Typically, this reaction is carried out at ambient temperature in the absence of solvent using equimolar amounts of aldehyde and anhydride in the presence of about 1 weight % acid (based on total weight of aldehyde and anhydride).

Referring to the second step in Scheme 1, there exist several well-known oxidizing agents which may be employed to form the epoxy moiety, such as for example, m-chloroperbenzoic acid. This reaction is typically carried out at about 0° C. in a suitable solvent. For optimum results, the ethylenically unsaturated gem-diester is typically added dropwise to a solution containing the oxidizing agent.

Presently preferred epoxidized derivatives of invention ethylenically unsaturated gem-diesters have the following structures:

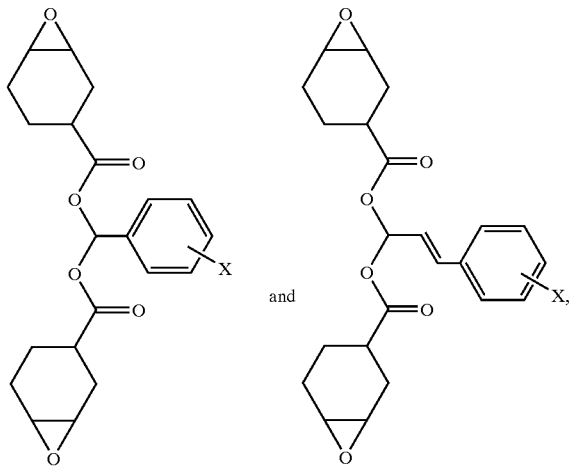

wherein X is hydrogen, alkyl, aryl, alkaryl, alkoxy, alkenyl, alkenyloxy, or halogen. In a presently most preferred aspect, X is hydrogen, chloride, or methyl. In addition, as described above, each R moiety may be substituted with a variety of substituents, such as, for example, alkyl, hydroxy, alkoxy, mercapto, cycloalkyl, substituted cycloalkyl, heterocyclic, substituted heterocyclic, aryl, substituted aryl, heteroaryl, substituted heteroaryl, aryloxy, substituted aryloxy, halogen, cyano, nitro, amino, amido, C(O)H, acyl, oxyacyl, carboxyl, carbamate, sulfonyl, sulfonamide, sulfuryl, and the like.

In accordance with the present invention, it has been discovered that when L is an aryl group, the temperature at which the gem-diester moiety is cleaved can be controlled by appropriate selection of substituents and/or substitution pattern on the aryl group. Thus, in accordance with the present invention, when rework is accomplished by application of appropriate temperature, the rework temperature can be tailored by appropriate choice of aromatic aldehyde in reaction 1 of Scheme 1. This is a significant benefit provided only by invention compounds and renders invention adhesive compositions adaptable to a wide range of applications.

A further advantage provided only by the present invention arises from the fact that the gem-diester moiety is both acid cleavable and base cleavable. Thus, when rework is accomplished under chemical means, reworking conditions can be tailored to meet a wide variety of applications. For example, in applications where treatment with even dilute acid may have deleterious effects, basic reworking conditions may be employed instead.

In some applications, it is desirable to employ invention compounds with more than two crosslinkable moieties (i.e., unit of ethylenic unsaturation or epoxide) per molecule. The increased crosslink density provided by such compounds often leads to improved physical properties such as, for example, increased adhesion and moisture resistance. Thus, in a still further embodiment of the present invention, there are provided tetra-epoxy derivatives of ethylenically unsaturated gem-diesters. Tetra-epoxy derivatives of ethylenically unsaturated gem-diesters can be readily prepared according to Scheme 1 by substituting a di-aldehyde for the mono-aldehyde in the first step of the synthesis outlined in Scheme 1. A preferred tetra-epoxy derivative of an ethylenically unsaturated gem-diester is shown below:

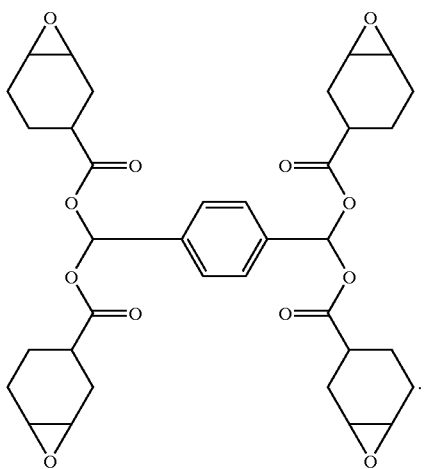

Referring to the exemplary structure shown above (wherein each R is cyclohexenyl and L is arylene), each R moiety and L may be substituted with a variety of substituents, such as, for example, alkyl, hydroxy, alkoxy, mercapto, cycloalkyl, substituted cycloalkyl, heterocyclic, substituted heterocyclic, aryl, substituted aryl, heteroaryl, substituted heteroaryl, aryloxy, substituted aryloxy, halogen, cyano, nitro, amino, amido, C(O)H, acyl, oxyacyl, carboxyl, carbamate, sulfonyl, sulfonamide, sulfuryl, and the like.

In accordance with yet another embodiment of the present invention, there are provided adhesive compositions comprising epoxidized derivatives of ethylenically unsaturated gem-diesters, optionally an epoxide co-reactant, at least one polymerization promoter, and optionally, a filler. Invention adhesive compositions may comprise only epoxidized derivatives of ethylenically unsaturated gem-diesters as the crosslinking monomer alone or may be used in combination with other epoxide co-reactants. When epoxide co-reactants are used, invention epoxidized gem-diesters comprise at least about 10 weight % of the total composition. Preferably, the epoxidized gem-diesters comprise at least about 25 weight % of the total composition. Most preferably, the epoxidized gem-diesters comprise at least about 50 weight % of the total composition. Epoxy co-reactants contemplated for optional use in the practice of the present invention include, for example, glycidyl ethers, glycidyl esters, cycloaliphatic epoxides, glycidyl amines, and the like. Presently preferred epoxy co-reactants contemplated for optional use in the practice of the present invention include bisphenol A diglycidyl ether, bisphenol F diglycidyl ether, butanediol diglycidyl ether, neopentyl glycol diglycidyl ether, epoxidized novolac resins, diglycidyl ortho-phthalate, diglycidyl para-phthalate, hydrogenated diglycidyl ortho-phthalate, 3,4-epoxycyclohexylmethyl-3,4-epoxycyclohexane carboxylate, aniline diglycidyl ether, and the like.

In accordance with a further embodiment of the present invention, there are provided adhesive compositions comprising ethylenically unsaturated gem-diesters, optionally a co-reactant, at least one polymerization promoter, and optionally, a filler. Invention adhesive compositions may comprise only ethylenically unsaturated gem-diesters as the crosslinking monomer alone or may be used in combination with other co-reactants. When co-reactants are used, invention ethylenically unsaturated gem-diesters comprise at least about 10 weight % of the total composition. Preferably, the ethylenically unsaturated gem-diesters comprise at least about 25 weight % of the total composition. Most preferably, the ethylenically unsaturated gem-diesters comprise at least about 50 weight % of the total composition. Co-reactants contemplated for optional use in conjunction with ethylenically unsaturated gem-diesters include compounds which can be copolymerized with olefins, such as for example, acrylates, maleimides, styrenes, and the like.

As employed herein, the term "polymerization promoter" refers to curing agents, co-curing agents, catalysts, initiators or other additives designed to participate in or promote curing of the adhesive formulation. With respect to epoxide-based adhesive formulations, such polymerization promoters include curing agents and catalysts such as, for example, anhydrides, amines, imidazoles, thiols, carboxylic acids, phenols, dicyandiamide, urea, hydrazine, hydrazide, amino-formaldehyde resins, melamine-formaldehyde resins, amine-boron trihalide complexes, quaternary ammonium salts, quaternary phosphonium salts, tri-aryl sulfonium salts, di-aryl iodonium salts, diazonium salts, and the like. Presently preferred curing agents and catalysts for epoxide-based formulations include anhydrides, amines, imidazoles, and the like. With respect to adhesive formulations comprising ethylenically unsaturated gem-diesters, such polymerization promoters include curing agents and catalysts such as, for example, free-radical curing agents (e.g., peroxides), hydrosilation agents, polythiols, and the like.

Initiators contemplated for use with epoxide-based adhesive formulations include hydroxy functionalized compounds such as, for example, alkylene glycols. Preferred alkylene glycols include ethylene glycols and propylene glycols.

Fillers contemplated for optional use in the practice of the present invention may optionally be conductive (electrically and/or thermally). Electrically conductive fillers contemplated for use in the practice of the present invention include, for example, silver, nickel, gold, cobalt, copper, aluminum, graphite, silver-coated graphite, nickel-coated graphite, alloys of such metals, and the like, as well as mixtures thereof. Both powder and flake forms of filler may be used in the adhesive compositions of the present invention. Preferably, the flake has a thickness of less than about 2 microns, with planar dimensions of about 20 to about 25 microns. Flake employed herein preferably has a surface area of about 0.15 to 5.0 m$^2$/g and a tap density of about 0.4 up to about 5.5 g/cc. It is presently preferred that powder employed in the practice of the invention has a diameter of about 0.5 to 15 microns. If present, the filler typically comprises in the a range of about 30% up to about 70% by weight of the adhesive formulation.

Thermally conductive fillers contemplated for optional use in the practice of the present invention include, for example, aluminum nitride, boron nitride, silicon carbide, diamond, graphite, beryllium oxide, magnesia, silica, alumina, and the like. Preferably, the particle size of these fillers will be about 20 microns. If aluminum nitride is used as a filler, it is preferred that it be passivated via an adherent, conformal coating (e.g., silica, or the like).

Electrically and/or thermally conductive fillers are optionally (and preferably) rendered substantially free of catalytically active metal ions by treatment with chelating agents, reducing agents, nonionic lubricating agents, or mixtures of such agents. Such treatment is described in U.S. Pat. No. 5,447,988, which is incorporated by reference herein in its entirety.

Optionally, a filler may be used that is neither an electrical nor thermal conductor. Such fillers may be desirable to impart some other property to the adhesive formulation such as, for example, reduced thermal expansion of the cured adhesive, reduced dielectric constant, improved toughness, increased hydrophobicity, and the like. Examples of such fillers include perfluorinated hydrocarbon polymers (i.e., TEFLON™), thermoplastic polymers, thermoplastic elastomers, mica, fused silica, glass powder, and the like.

Flexibilizers contemplated for optional use in the practice of the present invention include branched polyalkanes or polysiloxanes that lower the $T_g$ of the formulation. Such flexibilizers include, for example, polyethers, polyesters, polythiols, polysulfides, and the like. If present in the adhesive formulation, flexibilizers typically comprise in the range of about 0% up to about 30% by weight of the formulation.

Dyes contemplated for optional use in the practice of the present invention include nigrosine, Orasol blue GN, phthalocyanines, and the like. When used, organic dyes in relatively low amounts (i.e., amounts less than about 0.2 weight %) provide contrast.

Pigments contemplated for optional use in the practice of the present invention include any particulate material added solely for the purpose of imparting color to the formulation, e.g., carbon black, metal oxides (e.g., $Fe_2O_3$, titanium oxide), and the like. When present, pigments are typically present in the range of about 0.5 up to about 5 weight %, relative to the weight of the base formulation.

The decomposition of conventional epoxide-based thermoset adhesives generally occurs at temperatures in excess of 300° C. and these materials are therefore unsuitable for use in reworkable applications. In reworkable applications, it is required that cured adhesives withstand solder reflow temperatures without significant decomposition, i.e. at temperatures up to about 200° C. At the same time, it is required that the adhesives undergo rapid degradation at temperatures in the range of about 200 up to about 260° C.

Due to the labile gem-diester moiety distributed throughout the thermoset network, invention adhesive compositions may be readily reworked by heating to temperatures in the range of about 200° C. up to about 260° C. This allows bonded components to be easily separated from one another in a controlled and predictable manner. Indeed, the temperature at which invention adhesives become reworkable is determined by the structure of the gem-diester. Alternatively, invention adhesives may be reworked by treatment with dilute acid or dilute base. This alternative is particularly attractive in applications that may be sensitive to high temperature conditions. In addition, the versatility of gem-diester decomposition pathways provides great flexibility regarding choice of rework conditions. For example, there may be certain circumstances where chemical reworkability would be advantageously carried out using basic rather than acidic solutions.

Those of skill in the art recognize that many different electronic packages would benefit from preparation using the invention compositions described herein. Examples of such packages include ball grid arrays, super ball grid arrays, IC memory cards, chip carriers, hybrid circuits, chip-on-board, multi-chip modules, pin grid arrays, chip size packages (CSPs), and the like.

The invention will now be described in greater detail by reference to the following non-limiting examples.

EXAMPLES

Example 1

Synthesis of Epoxidized Gem-diester of Benzaldehyde and 3-Cyclohexene-1-anhydride Adduct

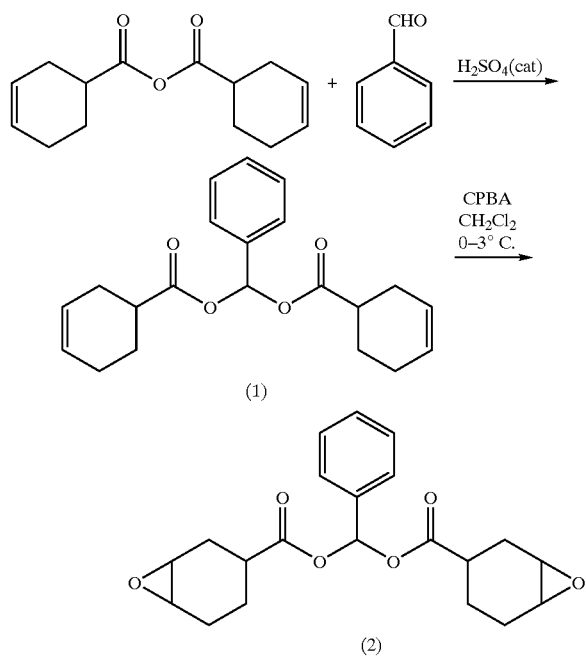

To a 100 mL, three-necked reaction flask fitted with a magnetic stirrer, thermocouple and addition funnel was added benzaldehyde (15.92 g; 0.15 moles) and 3-cyclohexene-1-anhydride (35.11 g; 0.15 moles). The mixture was stirred to obtain a homogeneous solution and concentrated sulfuric acid (0.05 g; 96%) was added. The solution turned a brown color on addition of the acid. The mixture was stirred for a further 4 hours at ambient temperature after which time the intermediate product, dicycloalkenyl gem-diester 1, was obtained in quantitative yield (51.03 g). The structure of the product was confirmed by $^1$H NMR analysis.

To a 1 L three-necked reaction flask, equipped with an addition funnel, magnetic stirrer, thermocouple and ice/water bath was added 3-chloroperoxybenzoic acid (CPBA) (74.15 g of 70% pure grade; 0.3 moles) and dichloromethane (500 mL). The mixture was stirred to dissolve the peroxy acid and the resultant solution cooled to about 1° C. A solution of the intermediate dicycloalkenyl gem-diester 1 (51.03 g; 0.15 moles) in dichloromethane (100 mL) was added dropwise over about 4 hours while maintaining the temperature between 0 and 3° C. The mixture was stirred for a further 16 hours during which time the temperature was allowed to slowly increase to ambient. The reaction mixture was filtered to remove solids, which were rinsed with dichloromethane (100 mL) and the combined filtrate and rinsings washed with 10% sodium sulfite solution (2×100 mL portions), saturated sodium bicarbonate solution (4×100 mL portions) and deionized water (3×150 mL portions). The washed solution was dried over anhydrous sodium sulfate, filtered and the solvent removed under reduced pressure to yield the epoxidized dicycloalkenyl gem-diester 2 as a yellow liquid (46.86 g; 84% yield). The structure of the product was confirmed by $^1$H NMR and IR spectral analysis.

Example 2

Synthesis of Epoxidized Gem-diester of p-Tolylaldehyde and 3-Cyclohexene-1-anhydride Adduct

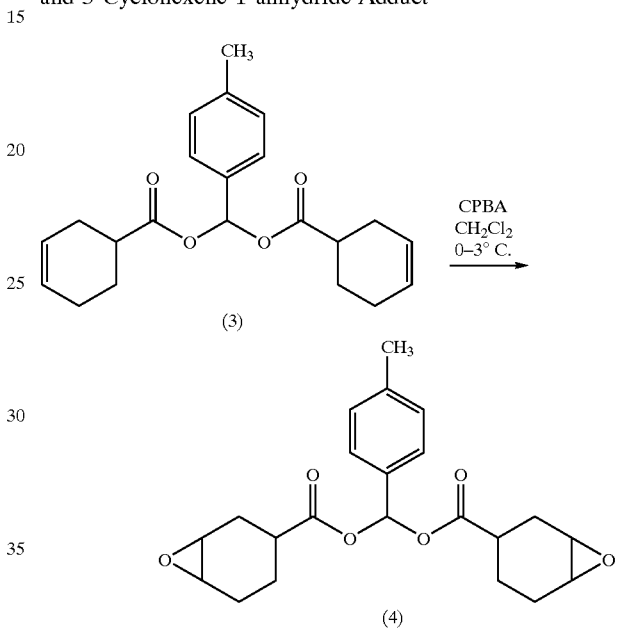

The synthesis and epoxidation of the dicycloalkenyl gem-diester of p-tolylaldehyde and 3-cyclohexene-1-anhydride 3 were carried out by procedures similar to those described in Example 1. The epoxidized product 4 was isolated as a yellow liquid (59% yield). The structure of the intermediate 3 and final product 4 were confirmed by $^1$H NMR and IR spectral analysis.

Example 3

Synthesis of Epoxidized Gem-diester of p-Chlorobenzaldehyde and 3-Cyclohexene-1-anhydride Adduct

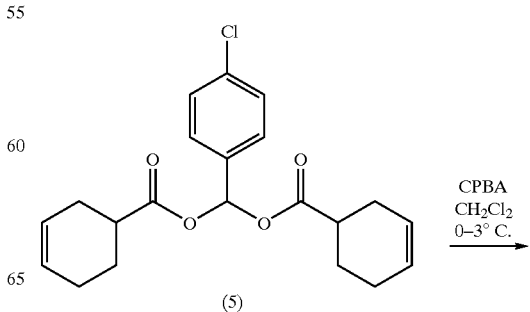

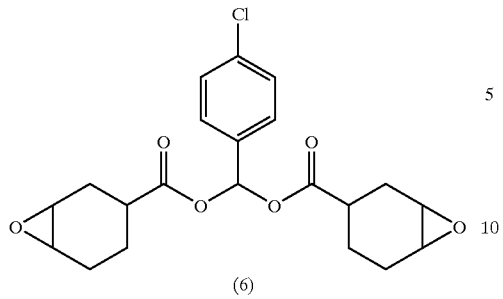

(6)

The synthesis and epoxidation of the dicycloalkenyl gem-diester of p-chlorobenzlaldehyde and 3-cyclohexene-1-anhydride 5 were carried out by procedures similar to those described in Example 1. The epoxidized product 6 was isolated as a yellow liquid (65% yield). The structures of the intermediate 5 and final product 6 were confirmed by $^1$H NMR and IR spectral analysis.

Example 4

Synthesis of Epoxidized Gem-diester of Cinnamaldehyde and 3-Cyclohexene-1-anhydride Adduct

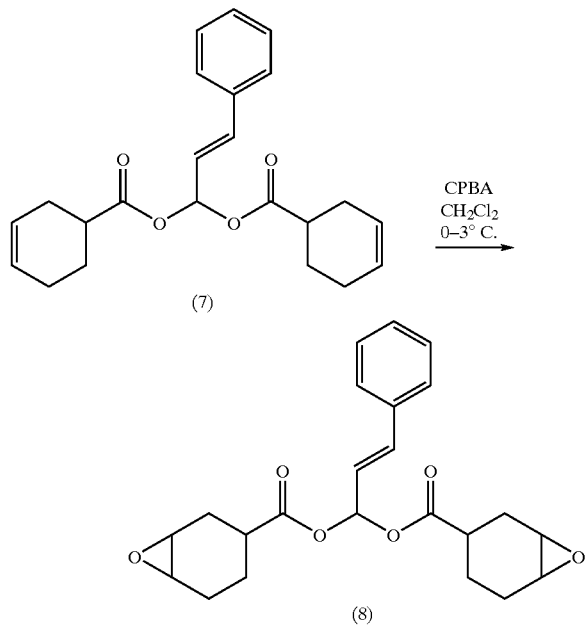

The synthesis and epoxidation of the dicycloalkenyl gem-diester of cinnamaldehyde and 3-cyclohexene-1-anhydride 7 were carried out by procedures similar to those described in Example 1. Phosphorous trichloride, rather than sulfuric acid, was used as catalyst for the synthesis of the intermediate 7. The epoxidized product 8 was isolated directly from the reaction mixture (71% yield). The structures of the intermediate 7 and final product 8 were confirmed by $^1$H NMR and IR spectral analysis and confirmed that epoxidation of the vinyl benzene double bond group did not occur.

Example 5
Synthesis of Epoxidized Gem-diester of Terephthalaldehyde and 3-Cyclohexene-1-anhydride Adduct

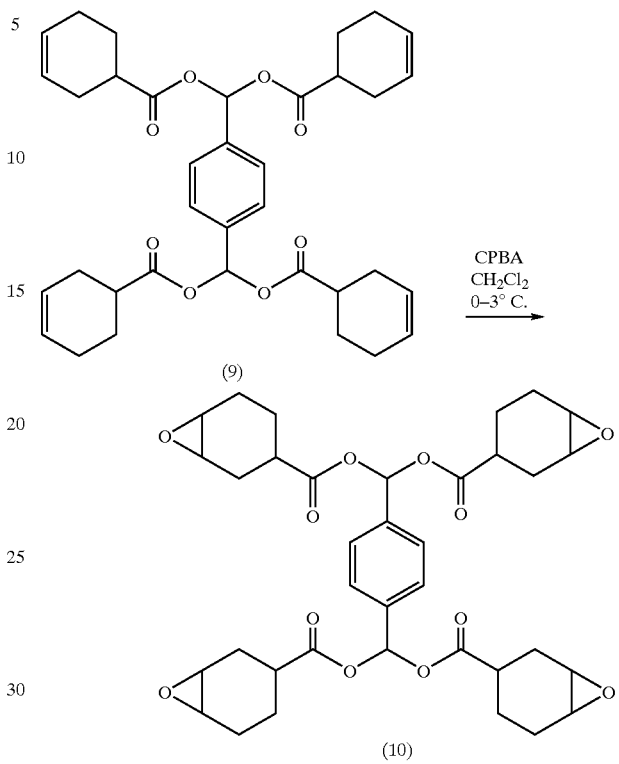

The synthesis and epoxidation of the tetracycloalkenyl bis gem-diester of terephthalaldehyde and 3-cyclohexene-1-anhydride 9 were carried out by procedures similar to those described in Example 1. In this case, two equivalents of anhydride per equivalent of aldehyde were used in the synthesis of the intermediate 9 and 4 equivalents of CPBA per equivalent of intermediate were used in the epoxidation step. The tetra-functional epoxidized product 10 was isolated as a paste-like substance (68% yield). The structures of the intermediate 9 and final product 10 were confirmed by $^1$H NMR and IR spectral analysis.

In the following Examples 6–8, the effect of the para-substituent on the aryl ring on thermal decomposition parameters is demonstrated.

Example 6
Thermal Decomposition Analysis of Formulation Containing Epoxidized Gem-diester 2

A heat curable epoxy adhesive composition was prepared by blending together gem-diester epoxide 2 (see Example 1), anhydride curing agent hexahydro-4-methylphthalic anhydride (HHMPA), polymerization initiator ethylene glycol (EG) and catalyst, N,N-dimethylbenzylamine (DBA), according to the formulation in Table 1. The anhydride/epoxy equivalent weight ratio=0.78

TABLE 1

| Component | Molecular weight | Weight % | Mole Fraction |
|---|---|---|---|
| Epoxide 2 | 372 | 57.5 | 0.37 |
| HHMPA | 168 | 40.9 | 0.58 |
| EG | 62 | 0.9 | 0.04 |
| DBA | 135 | 0.7 | 0.01 |

Samples of the formulation (8–10 mg) were hermetically sealed in aluminum DSC sample pans and cured by heating at 103° C. for 72 hours followed by a post-cure at 140° C. for 3 hours. DSC analysis was then performed on the cured samples over the temperature range −20 to +200° C. (heating rate 20° C./ minute), from which the initial Tg was found to be 152° C. (average of three measurements). The samples were then heated under isothermal conditions at temperatures typically employed for reworking and the change in Tg (ΔTg) determined as a function of the heating time. The results, for temperatures in the range 170–250° C., are presented in FIG. 1.

At 170° C., the Tg remained constant during the first five minutes of heating. This indicates that the cured adhesive is thermally stable at this temperature and no degradation of the network had occurred. At 200° C., a moderate decrease in glass transition was observed and the rate of decrease was essentially constant over a 5 minute heating period, indicating that network breakdown is occurring slowly, but steadily at this temperature. At 230° C., the decrease in Tg occurred more rapidly such that the breakdown of the network structure was almost complete within the first 2 minutes of heating. At 250° C., decomposition was complete within the first minute of heating. Additional heating results in little or no further change in Tg. These results demonstrate that the adhesive composition containing epoxide 2 is suitable for reworking at temperatures in the range 230–250° C.

Example 7
Thermal Decomposition Analysis of Formulation Containing Epoxidized Gem-diester 4

A heat curable epoxy adhesive composition was prepared by blending together gem-diester epoxide 4 (see Example 2) with curing agent, polymerization initiator and catalyst as described in Example 6. The formulation details are presented in Table 2. The anhydride/epoxy equivalent weight ratio=0.78

TABLE 2

| Component | Molecular Weight | Weight % | Mole Fraction |
|---|---|---|---|
| Epoxide 4 | 386 | 58.4 | 0.37 |
| HHMPA | 168 | 40.0 | 0.58 |
| EG | 62 | 0.9 | 0.04 |
| DBA | 135 | 0.7 | 0.01 |

Figure 2:
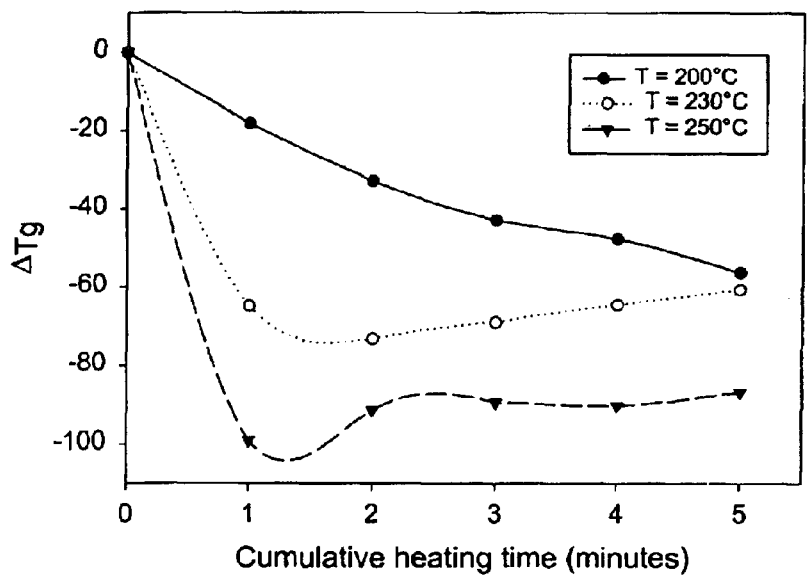
FIG. 2 illustrates the decomposition of anhydride cured formulation comprising invention compound 4 as a function of heating time at various temperatures (initial Tg=140° C.).

The adhesive formulation was cured and subjected to DSC analysis as described in Example 6 and the data is presented in FIG. 2. The initial Tg was found to be 140° C. (average of three measurements). The results at 200, 230 and 250° C. are presented in FIG. 2 and show that this composition has a similar decomposition profile to that of the formulation of Example 6. Since each of these formulations contain the same stoichiometric balance of monomer, curing agent, initiator and catalyst, it can be concluded that the 4-methyl group substituent derived from tolylaldehyde in epoxide 4 has the effect of reducing the cured Tg by 12° C.

These results demonstrate that the adhesive composition containing epoxide 4 is suitable for reworking at temperatures in the range 230–250° C. The network decomposition is complete after 1 minute at 250° C.

Example 8
Thermal Decomposition Analysis of Formulation Containing Epoxidized Gem-diester 6

A heat curable epoxy adhesive composition was prepared by blending gem-diester epoxide 6 (see Example 3) together with curing agent, polymerization initiator and catalyst as described in Example 6. The formulation details are presented in Table 3. The anhydride/epoxy equivalent weight ratio=0.78

TABLE 3

| Component | Molecular weight | Weight % | Mole Fraction |
|---|---|---|---|
| Epoxide 6 | 406.5 | 59.6 | 0.37 |
| HHMPA | 168 | 38.9 | 0.58 |
| EG | 62 | 0.9 | 0.04 |
| DBA | 135 | 0.6 | 0.01 |

Figure 3:
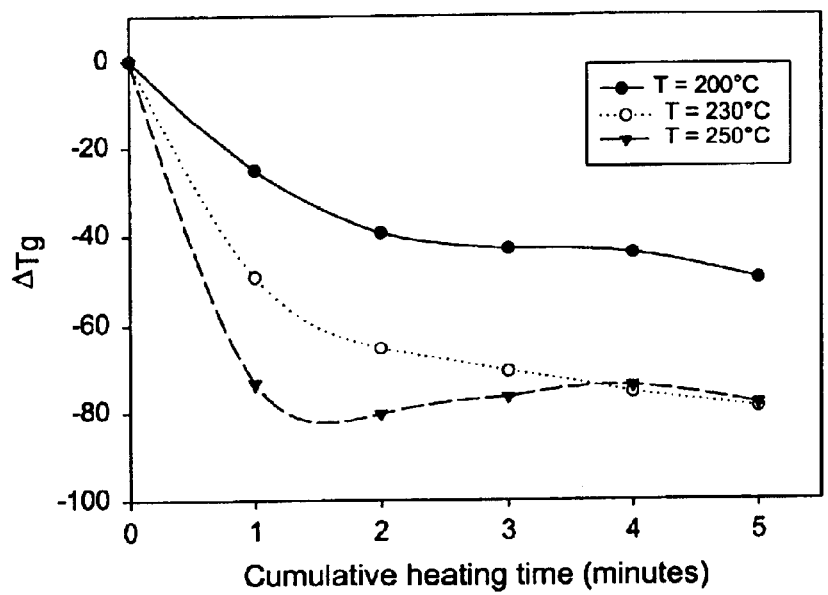
FIG. 3 illustrates the decomposition of anhydride cured formulation comprising invention compound 6 as a function of heating time at various temperatures (initial Tg=117° C.).

The adhesive formulation was cured and subjected to DSC analysis as described in Example 6 and the data is presented in FIG. 3. The initial Tg was found to be 117° C. (average of three measurements). The results at 200, 230 and 250° C. are presented in FIG. 3 and show that this compositions has a similar decomposition profile to formulations comprising epoxide 2 and epoxide 4.

Since the formulation containing epoxide 6 contains the same stoichiometric balance of monomer, curing agent, initiator and catalyst as the formulations containing epoxides 2 and 4, it can be concluded that the 4-chloro substituent of the phenyl group has the effect of further reducing the initial Tg of the cured adhesive. These results demonstrate that the adhesive composition containing epoxide 6 is suitable for reworking at temperatures in the range 230–250° C. Network decomposition is complete after one minute of heating at 250° C.

Example 9
Thermal Decomposition Analysis of Formulation Containing Epoxidized Gem-diester A heat curable epoxy adhesive composition was prepared by blending gem-diester epoxide 8 (see Example 4) together with curing agent, polymerization initiator and catalyst as described in Example 6. The formulation details are presented in Table 4. The anhydride/epoxy equivalent weight ratio=0.78

TABLE 4

| Component | Molecular weight | Weight % | Mole Fraction |
|---|---|---|---|
| Epoxide 8 | 398 | 59.0 | 0.37 |
| HHMPA | 168 | 39.4 | 0.58 |
| EG | 62 | 0.9 | 0.04 |
| DBA | 135 | 0.7 | 0.01 |

Figure 4:
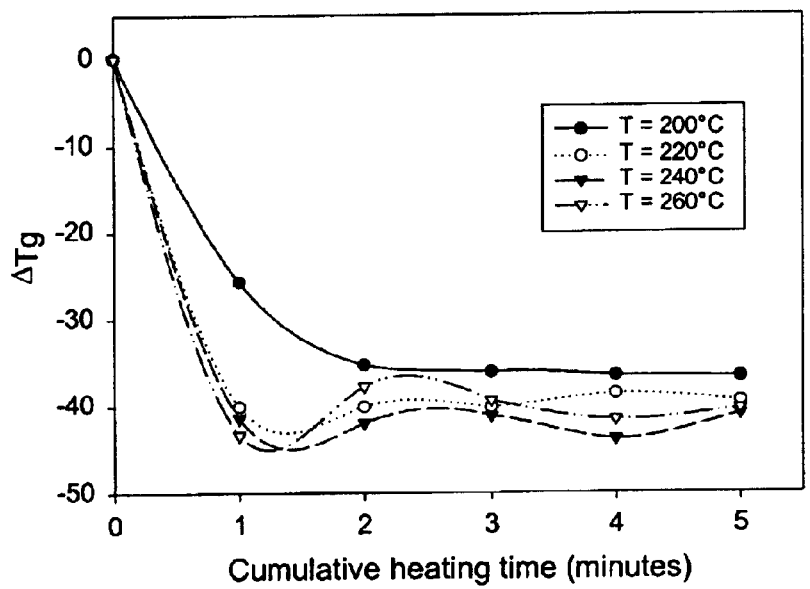
FIG. 4 illustrates the decomposition of anhydride cured formulation comprising invention compound 8 as a function of heating time at various temperatures (initial Tg=101° C.).

The adhesive formulation was cured and subjected to DSC analysis as described in Example 6. The initial Tg was found to be 101° C. (average of four measurements). The results at 200, 220, 240 and 260° C. are presented in FIG. 4. This material decomposes at a lower temperature than the formulations of Examples 6–8, with complete decomposition occurring within one minute at 220° C. The differences in decomposition temperature and Tg may be attributed to the different substituents on the alkyl portion of the ester monomer. This product may be reworked at temperatures in the range 200–220° C.

Example 10
Thermal Decomposition Analysis of Formulation Containing Epoxidized bis-Gem-diester 10

A heat curable epoxy adhesive composition was prepared by blending bis-gem-diester epoxide 10 (see Example 5) and gem-diester epoxide 2 (see Example 1), together with curing agent, polymerization initiator and catalyst as described in Example 6. In this example, epoxide 2 was used as a reactive diluent to ensure that the anhydride, initiator and catalyst were filly dissolved. The formulation details are presented in Table 5. The Anhydride/epoxy equivalent weight ratio=0.79.

TABLE 5

| Component | Molecular weight | Weight % | Mole Fraction |
|---|---|---|---|
| Epoxide 10 | 666 | 21.1 | 0.08 |
| Epoxide 2 | 372 | 35.3 | 0.24 |
| HHMPA | 168 | 41.9 | 0.63 |
| EG | 62 | 1.0 | 0.04 |
| DBA | 135 | 0.7 | 0.01 |

A sample of the adhesive formulation was cured and subjected to DSC analysis as described in Example 6. The initial glass transition Tg was found to occur at 154° C. The sample was heated under isothermal conditions at 250° C. for one minute and the Tg again determined by dynamic DSC as described in Example 6. The final Tg value was found to be 42° C., corresponding to a glass transition reduction of 112° C. This result is indicative of essentially complete destruction of the original network and makes the formulation EGD-10 particularly suitable for use as a thermally reworkable adhesive.

Example 11 (Comparative)
Thermal Decomposition Analysis of Formulation Containing Conventional bis-Cycloaliphatic Epoxide Ester ERL-4221 Cured With Anhydride For comparison purposes, an adhesive composition similar to those described in Examples 6–10 was prepared from a commercially available epoxide monomer 3,4-epoxycyclohexylmethyl 3,4-epoxycyclohexane-carboxylate (ERL-4221), supplied by Union Carbide Corporation. This monomer is structurally similar to the monomers of Examples 6–10 having cycloaliphatic epoxide groups. However, unlike invention epoxidized gem-diester monomers, the epoxide groups of ERL-4221 are linked together by a conventional mono-ester rather than a gem-diester group. The formulation details are presented in Table 6.

TABLE 6

ERL-4221 formulation.
Anhydride/epoxy equivalent weight ratio = 0.75

| Component | Molecular weight | Weight % | Mole Fraction |
|---|---|---|---|
| ERL-4221 | 252 | 49.2 | 0.38 |
| HHMPA | 168 | 48.9 | 0.57 |
| EG | 62 | 0.8 | 0.03 |
| DBA | 135 | 1.1 | 0.02 |

Figure 5:
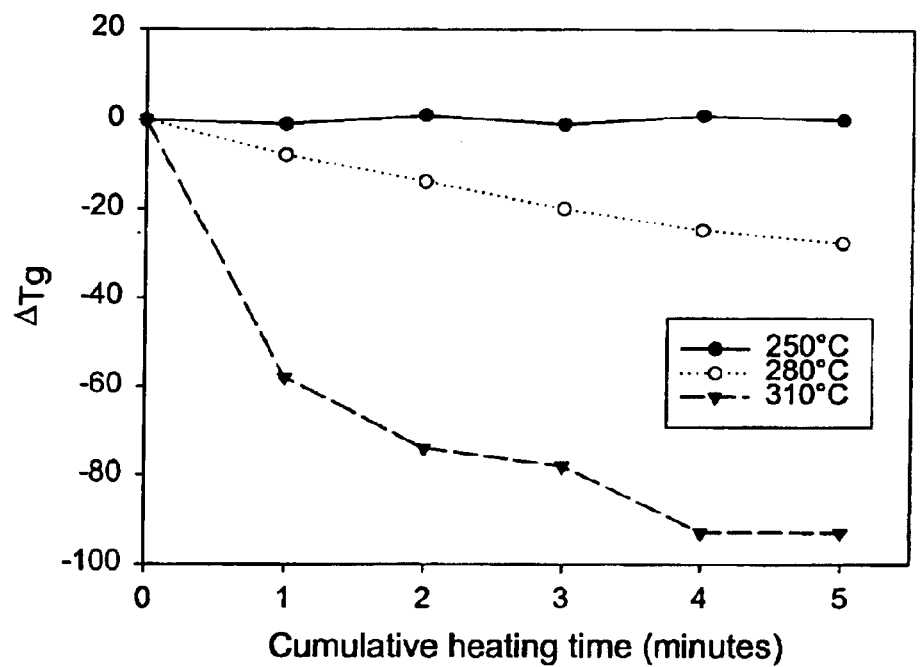
FIG. 5 illustrates decomposition of anhydride cured ERL-4221 formulation as a function of heating time at various temperatures (initial Tg=196° C.).

The adhesive formulation of Table 6 was cured and subjected to DSC analysis as described in Example 6. The results, presented in FIG. 5, show that the product exhibits no decomposition at 250° C. and only a small decomposition at 280° C. In fact, temperatures in excess of 300° C. are needed before there is a sufficient reduction in the glass transition to permit reworking of an adhesive that is based exclusively on ERL-4221 epoxy monomer.

While the invention has been described in detail with reference to certain preferred embodiments thereof, it will be understood that modifications and variations are within the spirit and scope of that which is described and claimed.

What is claimed is:
1. A gem-diester having the structure:

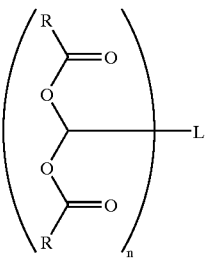

wherein:

L is optionally substituted hydrocarbyl or hydrocarbylene, each R is independently selected from optionally substituted hydrocarbyl or heteroatom-containing hydrocarbyl, and n is 1 or 2, with the proviso that said gem-diester has at least two units of ethylenic unsaturation.

2. A gem-diester according to claim 1, wherein L is optionally substituted hydrocarbyl.

3. A gem-diester according to claim 2, wherein L is optionally substituted aryl.

4. A gem-diester according to claim 3, wherein L is:

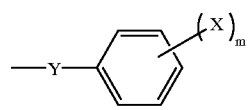

wherein:

Y is optional and if present is $C_1$ to $C_6$ alkylene or alkenylene,

X, when present, is alkyl, alkenyl, haloalkyl, hydroxy, alkoxy, mercapto, heterocyclic, aryl, alkaryl, alkenyloxy, heteroaryl, aryloxy, halogen, cyano, nitro, amino, amido, C(O)H, acyl, oxyacyl, carboxyl, carbamate, sulfonyl, sulfonamide, or sulfuryl, and m is 0–5.

5. A gem-diester according to claim 4 wherein m is 0.

6. A gem-diester according to claim 5 wherein each R is cycloalkenyl.

7. A gem-diester according to claim 4 wherein X is alkyl, alkenyl alkenyloxy, aryl, or alkaryl.

8. A gem-diester according to claim 7 wherein each R is cycloalkenyl.

9. A gem-diester according to claim 1 wherein n is 2.

10. A gem-diester according to claim 9, wherein each R is cycloalkenyl.

11. A gem-diester according to claim 1, wherein L is optionally substituted aliphatic hydrocarbyl.

12. A gem-diester according to claim 11, wherein L is optionally substituted alkyl, alkenyl, cycloalkyl or cycloalkenyl.

13. A derivative of a gem-diester according to claim 1, wherein said units of ethylenic unsaturation are epoxidized.

14. A derivative of a gem-diester according to claim 4, wherein said units of ethylenic unsaturation are epoxidized.

15. An epoxidized derivative of a gem-diester according to claim 6 having the following structure:

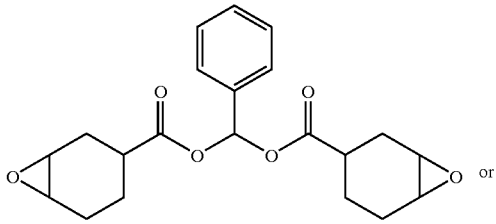

or

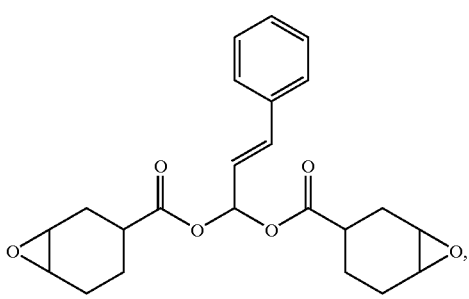

or a ring-substituted derivative thereof.

16. An epoxidized derivative of a gem-diester according to claim 8 having the following structure:

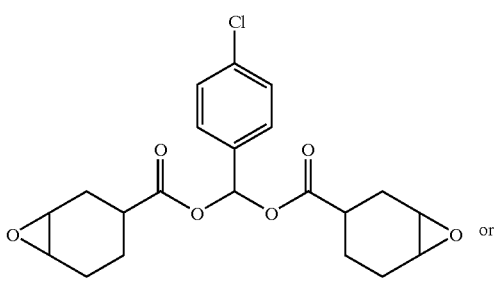

or

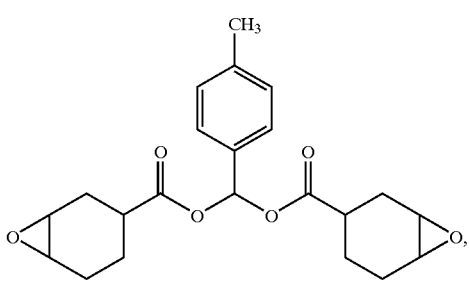

or a ring-substituted derivative thereof.

17. An epoxidized derivative of a gem-diester according to claim 10 having the structure:

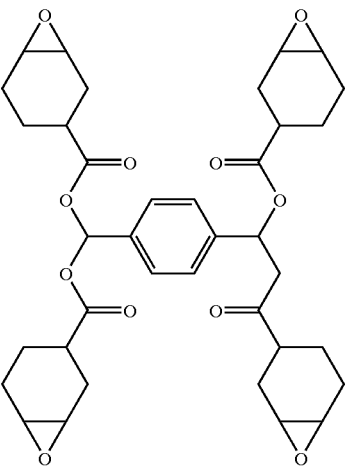

or a ring-substituted derivative thereof.

18. An adhesive composition comprising a gem-diester according to claim 1, at least one polymerization promoter, and optionally, a filler.

19. An adhesive composition comprising a gem-diester according to claim 4, at least one polymerization promoter, and optionally, a filler.

20. An adhesive composition according to claim 19, wherein said polymerization promoter is a free-radical curing agent, a hydrosilation agent, or a polythiol.

21. An adhesive composition according to claim 20, wherein said polymerization promoter is a free-radical curing agent.

22. An adhesive composition according to claim 21, wherein said free-radical curing agent is a peroxide.

23. An adhesive composition comprising a compound according to claim 13, at least one polymerization promoter, and optionally, a filler.

24. An adhesive composition comprising a compound according to claim 23, comprising at least two polymerization promoters.

25. An adhesive composition according to claim 24, wherein said polymerization promoters are curing agents, catalyst, or initiators.

26. An adhesive composition according to claim 25, wherein said curing agent is an anhydride, imidazole, amine, or carboxylic acid.

27. An adhesive composition according to claim 25, wherein said catalyst is an amine, hydrazine, dicyandiamide, or urea.

28. An adhesive composition according to claim 25, wherein said initiator is an alkylene glycol.

29. An adhesive composition according to claim 28, wherein said alkylene glycol is ethylene glycol or propylene glycol.

30. An adhesive composition comprising an epoxide compound according to claim 14, at least one polymerization promoter, and optionally, a filler.

31. An adhesive composition comprising an epoxide compound according to claim 30, comprising at least two polymerization promoters.

32. An adhesive composition according to claim 31, wherein said polymerization promoters are curing agents, catalysts, or initiators.

33. An adhesive composition according to claim 32, wherein said curing agent is an anhydride, imidazole, amine, or carboxylic acid.

34. An adhesive composition according to claim 32, wherein said catalyst is an amine, hydrazine, dicyandiamide, or urea.

35. An adhesive composition according to claim 32, wherein said initiator is an alkylene glycol.

36. An adhesive composition according to claim 35, wherein said alkylene glycol is ethylene glycol or propylene glycol.

37. An adhesive composition according to claim 24, wherein said polymerization promoters comprise in the range of about 0.1 weight % up to about 1.0 weight % of the total composition.

38. An adhesive composition according to claim 37, wherein said polymerization promoters comprise in the range of about 0.1 weight % up to about 0.5 weight % of the total composition.

39. An adhesive composition according to claim 23, wherein reaction products of said composition are reworkable.

40. An adhesive composition according to claim 30, wherein reaction products of said composition are reworkable.

41. An adhesive composition according to claim 23, wherein reaction products of said composition are acid-cleavable.

42. An adhesive composition according to claim 23, wherein reaction products of said composition are base-cleavable.

43. An adhesive composition according to claim 30, wherein reaction products of said composition are acid-cleavable.

44. An adhesive composition according to claim 30, wherein reaction products of said composition are base-cleavable.

45. An adhesive composition according to claim 23, wherein reaction products of said composition ar thermally cleavable.

46. An adhesive composition according to claim 30, wherein reaction products of said composition are thermally cleavable.

47. An adhesive composition according to claim 23, further comprising a reactive diluent.

48. An adhesive composition according to claim 30, further comprising a reactive diluent.

49. A method for adhesively attaching a device to a substrate, said method comprising dispensing an adhesive composition according to claim 23 onto a substrate and/or a device or between said substrate and said device to form an assembly, and exposing the assembly to conditions sufficient to cure the adhesive.

50. A method for removing an adhesively attached device from a substrate, said method comprising exposing an adhesive composition according to claim 23 positioned between said substrate and said device to temperatures in the range of about 200° C. up to about 260° C., and removing said device from said substrate.

51. A method for adhesively attaching a first article to a second article, said method comprising:
(a) applying a composition according to claim 23 to said first article,
(b) bringing said first and second article into intimate contact to form an assembly wherein said first article and said second article are separated only by the adhesive composition applied in step (a), and thereafter,
(c) subjecting said assembly to conditions suitable to cure said adhesive composition.

52. An assembly comprising a first article reversibly adhered to a second article by cured reaction products of the adhesive composition according to claim 23.

53. An assembly produced by the method according to claim 49.

54. An assembly produced by the method according to claim 51.

55. A method for the preparation of an epoxidized gem-diester, comprising
a) contacting an aldehyde with an anhydride, wherein the aldehyde and the anhydride combined have at least two units of ethylenic unsaturation, in the presence of an acid under conditions suitable to allow an addition reaction to occur between said aldehyde and said anhydride, and
b) contacting the product of step (a) with an oxidizing agent under conditions suitable to epoxidize said units of ethylenic unsaturation.

56. A gem-diester having the structure:

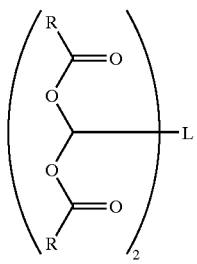

wherein:
L is optionally substituted hydrocarbyl, hydrocarbylene, heteroatom-containing hydrocarbyl, or heteroatom-containing hydrocarbylene, and
each R is independently selected from optionally substituted hydrocarbyl or heteroatom-containing hydrocarbyl,
with the proviso that said gem-diester has at least two units of ethylenic unsaturation.

57. A gem-diester according to claim 56, wherein L is optionally substituted hydrocarbyl.

58. A gem-diester according to claim 57, wherein L is optionally substituted aryl.

59. A gem-diester according to claim 58, wherein L is:

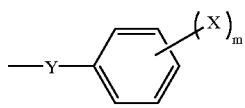

wherein:
Y is optional and if present is $C_1$ to $C_6$ alkylene or alkenylene,
X, when present, is alkyl, alkenyl, haloalkyl, hydroxy, alkoxy, mercapto, heterocyclic, aryl, alkaryl, alkenyloxy, heteroaryl, aryloxy, halogen, cyano, nitro, amino, amido, C(O)H, acyl, oxyacyl, carboxyl, carbamate, sulfonyl, sulfonamide, or sulfuryl, and
m is 0–5.

60. A gem-diester according to claim 59 wherein m is 0.

61. A gem-diester according to claim 60 wherein each R is cycloalkenyl.

62. A gem-diester according to claim 59 wherein X is alkyl, alkenyl, alkenyloxy, aryl, or alkaryl.

63. A gem-diester according to claim 62 wherein each R is cycloalkenyl.

64. A gem-diester according to claim 56, wherein L is optionally substituted aliphatic hydrocarbyl.

65. A gem-diester according to claim 64, wherein L is optionally substituted alkyl, alkenyl, cycloalkyl, or cycloalkenyl.

* * * * *